(12) United States Patent
Scavone et al.

US006352688B1

(10) Patent No.: US 6,352,688 B1
(45) Date of Patent: *Mar. 5, 2002

(54) HIGH EFFICACY, LOW RESIDUE ANTIPERSPIRANT STICK COMPOSITIONS

(75) Inventors: Timothy Alan Scavone, Loveland; James David Landgrebe, Madeira; Eric David Dodson, West Chester, all of OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/651,378

(22) Filed: Aug. 29, 2000

Related U.S. Application Data

(63) Continuation-in-part of application No. 09/573,031, filed on May 17, 2000, now abandoned.

(51) Int. Cl.$^7$ .............................. A61K 7/32; A61K 7/34; A61K 7/38; A61K 7/42; A61K 7/00
(52) U.S. Cl. .............................. 424/65; 424/59; 424/66; 424/68; 424/400; 424/401
(58) Field of Search .............................. 424/65, 66, 68, 424/59, 400, 401

(56) References Cited

U.S. PATENT DOCUMENTS

| | | | |
|---|---|---|---|
| 4,151,272 A | 4/1979 | Geary et al. | 424/68 |
| 5,102,656 A | 4/1992 | Kasat | 424/66 |
| 5,156,834 A | 10/1992 | Beckmeyer et al. | 424/47 |
| 5,250,291 A | 10/1993 | Park et al. | 424/66 |
| 5,449,511 A | 9/1995 | Coe | 424/66 |
| 5,500,209 A | 3/1996 | Ross et al. | 424/66 |
| 5,516,511 A | 5/1996 | Motley et al. | 424/65 |
| 5,650,144 A | 7/1997 | Hofrichter et al. | 424/66 |
| 5,718,890 A | 2/1998 | Putman et al. | 424/65 |
| 5,744,130 A | 4/1998 | Guskey et al. | 424/66 |
| 5,750,096 A | 5/1998 | Guskey | 424/65 |
| 5,776,494 A | 7/1998 | Guskey et al. | 424/484 |
| 5,833,964 A | 11/1998 | Linn et al. | 424/65 |
| 5,840,286 A | 11/1998 | Gardlik et al. | 424/65 |
| 5,840,288 A | 11/1998 | Guskey et al. | 424/65 |
| 5,885,559 A | 3/1999 | Lee et al. | 424/65 |
| 5,965,113 A | 10/1999 | Guskey | 424/66 |
| 5,976,514 A | 11/1999 | Guskey et al. | 424/65 |

FOREIGN PATENT DOCUMENTS

| | | |
|---|---|---|
| CA | 1 146 867 | 5/1983 |
| EP | 135315 | 4/1995 |
| GB | 2299024 A | 9/1996 |
| WO | WO 91/04009 | 4/1991 |
| WO | WO 99/16410 | 4/1999 |
| WO | WO 9951192 A2 | 10/1999 |

*Primary Examiner*—Shelley A. Dodson
(74) *Attorney, Agent, or Firm*—William J. Winter; Tara M. Rosnell; Steven W. Miller

(57) ABSTRACT

Disclosed are anhydrous antiperspirant sticks that comprise from about 0.5% to about 60% by weight of particulate antiperspirant active; from about 16% to about 50% by weight of a solid suspending agent; from about 10% to about 80% by weight of a volatile silicone; and from about 1% to about 35% by weight of a non volatile silicone, wherein the sticks are preferably substantially free of nonvolatile organic liquids having a C log P value greater than 5.5, and have a product hardness of at least about 600 gram·force. The sticks are further characterized by defined low residue and/or high antiperspirant efficacy measures. These compositions contain relatively high solid suspending agent concentrations of at least 16% by weight and still provide low residue performance and high antiperspirant efficacy.

64 Claims, No Drawings

HIGH EFFICACY, LOW RESIDUE ANTIPERSPIRANT STICK COMPOSITIONS

CROSS REFERENCE TO RELATED APPLICATION

This application is a continuation-in-part of prior application Ser. No. 09/573,031 filed on May 17, 2000 now abandoned.

TECHNICAL FIELD

The present invention relates to antiperspirant stick compositions that contain relatively high suspending agent concentrations, but that still provide low residue performance and high antiperspirant efficacy.

BACKGROUND OF THE INVENTION

There are many types of solid antiperspirant sticks that are commercially available or otherwise known in the antiperspirant art. These products typically contain an astringent material, e.g. zirconium or aluminum salts or combinations thereof, solubilized or dispersed in a suitable liquid carrier, and the solution or dispersion contained within a solid matrix that gives the product a solid stick form.

These solid antiperspirant sticks are ideally designed to provide effective perspiration and odor control while also being cosmetically acceptable during and after application onto the underarm area of the skin. In this context, cosmetically acceptable means that the product glides on smoothly during application, is non irritating, and results in little or no visible residue (e.g., low residue performance) after application to the skin.

Examples of solid antiperspirant sticks that provide good antiperspirant efficacy and low residue performance are described in U.S. Pat. No. 5,840,286 (Gardlik et al.) and U.S. Pat. No. 5,429,816 (Hofrichter et al.). Both disclose a variety of low residue antiperspirant sticks which contain an antiperspirant active, a suitable liquid carrier, and up to about 15% by weight of a low residue gellant such as 12-hydroxystearic acid or similar other materials.

Although low-residue solid antiperspirants with good antiperspirant efficacy such as those described by Gardlik et al. and Hofrichter et al. are now well known, these low-residue solids typically contain no more than about 15% by weight of a solid suspending agent. For some types of solid suspending agents, however, higher concentrations are needed in order to formulate a solid stick having the desired hardness and application rheology. Examples of such other suspending agents include a variety of solid triglycerides and other wax-like materials that generally require more than about 15% by weight. At these higher solid suspending agent concentrations, especially when formulated as a low-residue product, it becomes increasingly more difficult to maintain antiperspirant efficacy. It is known that many solid suspending agents at higher concentrations can inhibit release of antiperspirant active after application, and thus inhibit antiperspirant efficacy which is tied closely to antiperspirant release characteristics from the applied product matrix.

It has now been found that a low-residue antiperspirant stick can be formulated at solid suspending agent concentrations above 15% by weight of the composition, and still provide good antiperspirant efficacy. It has been found that by formulating the solid stick to provide low residue performance with a combination of volatile and nonvolatile silicones, solid antiperspirant active, and solid suspending agents, wherein the solid stick is preferably substantially free of any organic nonvolatile liquid having a C log P value greater than about 5.5, that a low residue, high-suspending agent concentration, solid stick can be formulated that also provides excellent antiperspirant efficacy. It has been found that the solid antiperspirant active is more effective when delivered from an anhydrous base containing a volatile and nonvolatile solvent that is also substantially free of relatively high C log P organic nonvolatile liquids. It is believed that this formulation allows for better release of antiperspirant active after application to the skin, and thus delivers improved antiperspirant efficacy even in the presence of relatively high solid suspending agent concentrations.

It is therefore an object of the present invention to provide a solid, low-residue, anhydrous antiperspirant stick that contains relatively high solid suspending agent concentrations but that still delivers improved antiperspirant efficacy.

SUMMARY OF THE INVENTION

The present invention is directed to anhydrous antiperspirant sticks comprising from about 0.5% to about 60% by weight of a particulate antiperspirant active; from about 16% to about 50% by weight of a solid suspending agent; from about 10% to about 80% by weight of a volatile silicone; and from about 1% to about 35% by weight of a non volatile silicone. The sticks are preferably substantially free of those nonvolatile organic liquids having a C log P value greater than 5.5. The sticks have a product hardness of at least about 600 gram·force and can be characterized in terms of low residue and/or high antiperspirant efficacy measures.

It has been found that, although these compositions can be formulated to contain relatively high concentrations of a solid suspending agent, they still provide improved low residue performance and high antiperspirant efficacy.

DETAILED DESCRIPTION OF THE INVENTION

The anhydrous, low-residue, antiperspirant stick compositions of the present invention comprise as essential ingredients particulate antiperspirant active, suspending agent, volatile silicone, and non volatile silicone. Each is described in detail hereinafter.

The term "anhydrous" as used herein means that the antiperspirant stick composition of the present invention, and the essential or optional components thereof are substantially free of added or free water. From a formulation standpoint, this means that the anhydrous antiperspirant stick compositions of the present invention preferably contain less than about 5%, more preferably less than about 3%, even more preferably less than about 1%, most preferably zero percent, by weight of free or added water, other than the water of hydration typically associated with the particulate antiperspirant active prior to formulation.

All melt points referenced herein, unless otherwise specified, are measured by well known technique of Differential Scanning Calorimetry (DSC). An example of this technique is described in U.S. Pat No. 5,306,514 (Letton et al.), which description is incorporated herein by reference.

The term "low residue" as used herein refers generally to the visible residue left on the applied areas of the skin during or immediately after application of an antiperspirant composition, and is used herein as a measure to help define the antiperspirant composition of the present invention. In this context, low residue measures include Tan Delta and Residue Grade values, each of which is determined separately in accordance with the Tan Delta and Residue Grade methodologies described hereinafter.

The term "ambient conditions" as used herein refers to surrounding conditions under about one (1) atmosphere of pressure, at about 50% relative humidity, and at about 25° C., unless otherwise specified. All values, amounts and measurements described herein are obtained under ambient conditions unless otherwise specified.

The term "volatile" as used herein refers to those materials which have a measurable vapor pressure at 25° C. Such vapor pressures will typically range from about 0.01 mmHg to about 6 mmHg, more typically from about 0.02 mmHg to about 1.5 mmHg, and have an average boiling point at one (1) atmosphere of pressure (atm) of less than about 250° C., more typically less than about 235° C. at one (1) atm. Conversely, the term "non volatile" refers to those materials which are not "volatile" as defined herein.

The term "skin temperature" as used herein refers to the temperature of the axilla area of the skin, which is generally at or slightly below a typical body temperature of about 37° C.

The anhydrous antiperspirant stick compositions of the present invention can comprise, consist of, or consist essentially of the essential elements and limitations of the invention described herein, as well as any additional or optional ingredients, components, or limitations known or otherwise effective for use in such compositions.

All percentages, parts and ratios are by weight of the total composition, unless otherwise specified. All such weights as they pertain to listed ingredients are based on the specific ingredient level and, therefore, do not include solvents, carriers, by-products, filler or other minor ingredients that may be included in commercially available materials, unless otherwise specified.

I. Product Characteristics

The anhydrous antiperspirant stick compositions of the present invention are defined in terms of an essential combination of ingredients and product characteristics, wherein the product characteristics include product hardness, Residue Grade, Tan Delta values, and/or Antiperspirant Efficacy Index. Each of these product characteristics is defined hereinafter in detail.

Hardness

The anhydrous antiperspirant stick compositions of the present invention have a product hardness of least about 600 gram·force, most typically from about 600 gram·force to about 5,000 gram·force, preferably from about 750 gram·force to about 2,000 gram·force, more preferably from about 800 gram·force to about 1,400 gram·force.

The term "product hardness" or "hardness" as used herein is a reflection of how much force is required to move a penetration cone a specified distance and at a controlled rate into an antiperspirant stick composition under the following test conditions. Higher values represent harder product, and lower values represent softer product. These values are measured at 27° C., 15% relative humidity, using a TA-XT2 Texture Analyzer, available from Texture Technology Corp., Scarsdale, N.Y., U.S.A. The product hardness value as used herein represents the peak force required to move a standard 45° angle penetration cone through the composition for a distance of 10 mm at a rate of 2 mm/second. The standard cone is available from Texture Technology Corp., as part number TA-15, and has a total cone length of about 24.7 mm, angled cone length of about 18.3 mm, a maximum diameter of the angled surface of the cone of about 15.5 mm. The cone is a smooth, stainless steel construction and weighs about 17.8 grams.

The product hardness is preferably selected for each antiperspirant stick formulation to help provide the desired application rheology, thus resulting in the desired low-residue application layer as applied to the skin. Although low-residue performance can be controlled by a variety of mechanisms known in the antiperspirant art, it is preferred in the compositions of the present invention that low-residue performance be accomplished, at least in part, by controlling product hardness.

Residue Grade

The antiperspirant stick compositions of the present invention provide low residue performance from a solid stick formulation. These compositions preferably have a Residue Grade of less than about 50, preferably less than about 40, more preferably less than about 35. In this context, the Residue Grade is an indirect measure of the visible residue that is likely to remain on the skin after topical application of the antiperspirant stick composition.

The Residue Grade as used to characterize preferred embodiments of the present invention is determined by the Naugahyde Method described herein. In accordance with this method, a piece of commercial, black, dull finished, small grained vinyl (Boltaflex vinyl upholstery, Prefixx protective finish, Mfr. GenCorp Polymer Products) cut to a 10 cm×15 cm rectangular strip is placed on a horizontal platform. Each corner of the vinyl strip is then secured with a small binder clip after the material has been slightly stretched to create a smooth surface. An antiperspirant stick under ambient conditions (for at least 24 hours prior to testing) is trimmed flat across the top of the container and placed on a balance which is then tared to 0.00 grams in order to determine the mass of product to be applied to the vinyl. The stick composition contained within and partially extending out 0.5 cm from a conventional antiperspirant stick package (5.2 cm×2.7 cm topographically oval package) is positioned perpendicular to and above the positioned vinyl by securing the container onto a movable mechanical arm, such that the flat, trimmed surface of the secured product extends out of the package and is facing parallel to the horizontally positioned vinyl. The antiperspirant stick is then slowly moved vertically toward the vinyl sample until the flat, trimmed surface of the product rests upon the far left area of the positioned vinyl . A weight is placed on the product sample so that all of the flat, trimmed surface of the product uniformly contacts the positioned vinyl during testing. The applied weight is selected so as to provide 45.3 grams/cm$^2$ to the trimmed surface of the product sample, eg., 500 gram weight applied to an oval 5.2 cm×2.7 cm trimmed surface area. The weighted sample is then manually moved repeatedly back and forth across the entire length of the piece of vinyl at a rate of one stroke per second (one stroke equals one left to right movement or one right to left movement), until 0.20 gms. ±0.02 gm. of product has been evenly applied over 15.24 cm×5.08 cm area of the black vinyl (0.0026 grams of product per cm$^2$ of the black vinyl surface). The product sample is then removed from the mechanical arm piece and weighed. The vinyl is then unclipped and carefully removed from the platform and dried down for 6 hours.

A calibrated Minolta CR-300 Chroma Meter (available from Minolta Corp., Ramsey, N.J., USA) is then used to measure the L-value (on the L, a, b color scale) of each of the applied vinyl surfaces. For each of the applied vinyl surfaces, twelve random, non-overlapping areas of the applied surface are measured for L-values by the Chroma Meter with its clear plastic view port removed to allow direct placement of the Meter port onto the vinyl so that the meter port is positioned over but without touching the applied vinyl surface. An average L-value is then determined for the twelve measurements which then corresponds to the Residue Grade as described herein.

Tan Delta

The antiperspirant stick compositions of the present invention preferably have mechanical properties defined in terms of selected Tan Delta values, wherein the compositions have a Tan Delta Value at 1 Hz of less than about 0.40, preferably less than 0.35, more preferably less than 0.30. These Tan Delta values are measured by Dynamic Mechanic Thermal Analysis (DMTA) in accordance with the following methodology.

The Tan Delta value as used herein is determined by Dynamic Mechanical Thermal Analysis (DMTA). In this analysis, a solid antiperspirant stick is subjected to a slight two-dimensional vertical force comprised of a static (constant) and dynamic (oscillating) component. Enough dynamic force is applied to generate 5 microns of spring amplitude before measuring how the antiperspirant stick structure responds as a function of the applied force, temperature or frequency changes. DMTA is used to determine a storage modulus value and a ratio of a loss modulus to storage modulus (Tan Delta value).

More specifically, Tan Delta values are measured using a Perkin Elmer Dynamic Mechanical Thermal Analysis (DMTA) instrument, Model DMA 7e, (available from Perkin Elmer Corporation, 761 Main Avenue, Norwalk, Conn., USA), fitted with a parallel plate fixture. The top plate (connected to the probe) is a 10 mm plate, while the bottom plate (on which the sample rests) is a 20 mm plate. The instrument is calibrated according to manufacturer instructions. The probe is calibrated using the Tare Probe function on the Pyris software. The sample is prepared by cutting from an antiperspirant stick a 6 mm (thick) by 10 mm wide section. The sample must be cut from the stick so that the sample thickness is uniformly 6 mm to obtain reliable and consistent measures. The cross section is then placed into the DMTA instrument into the parallel plate fixture arrangement, resting on the 20 mm plate. The probe is lowered (with no force applied) and the furnace is raised with the temperature set at 25° C. The forces are set as such: A static force of 1000 mn (millinewton) and a dynamic force of 800mn (millinewton) are used as the initial force at a constant frequency of 1 cycle/second (Hz). The constant amplitude function is set to maintain a constant amplitude of 5 microns, allowing the dynamic component to vary to meet this amplitude setting. If required (i.e. the dynamic component exceeds the static force and causes the probe to bounce), the static force range should be adjusted so that the DMTA can control the instrument at a constant 5 microns of amplitude. The capturing of the Tan Delta measurement should be started within one minute after applying the force component. The Tan Delta is then recorded over the space of 5 minutes. This is repeated with 5 different samples of the same material and the average recorded. This average value is then reported as the Tan Delta value as used herein.

It has been found that the antiperspirant compositions of the present invention are especially effective in providing low residue performance and aesthetics when formulated to have the above-defined Tan Delta Values. These compositions, when formulated within the defined range of Tan Delta values, apply more smoothly and with relatively less visible residue.

Antiperspirant Efficacy Index

The antiperspirant stick compositions of the present invention preferably provide improved antiperspirant efficacy, wherein the sticks have an Antiperspirant Efficacy Index of at least about 1.0 as determined by the following methodology.

To determine Antiperspirant Efficacy Index values, in accordance with the antiperspirant efficacy methodology described herein, at least thirty-two normal female test participants, ages 18 to 65 years, are subjected to a five week, pretreatment, conditioning period during which each participant does not apply or otherwise use any underarm antiperspirant and/or deodorant products.

After completing the five week pretreatment period, each test participant is then immediately subjected to a product treatment period over the next two weeks. Each participant is treated with a control antiperspirant product and a test antiperspirant product. Each of the products is randomly assigned and applied to either of the participants axillae, e.g, one product applied to the left axillae and the other product applied to the right axillae, and thereafter applied daily to the same assigned axillae for each particular test participant. The product and control treatments are delivered from their respective containers and evenly distributed over a 4×6 inch area centered on each axilla at the application rate of 0.40 grams of product per axillae. Subjects receive treatment applications for ten consecutive days.

Baseline sweat collections are taken for each test participant under defined hot room conditions approximately one day prior to the first product treatment. Post-treatment sweat collections are also taken under the same hot room conditions approximately 10–12 hours after the third (3 day) and tenth (10 day) days of product applications. Axillary sweating is induced in each test participant by placing them in a hot room maintained at 100° F.±2° F. with a relative humidity of 35%±5%.

Baseline sweat volumes and baseline axillary ratios are determined for the group of approximately test participants. Baseline volume is used to compare differences between the highest and lowest rates of sweating among all of the test participants. If the difference between the highest and lowest rates does not exceed 600 milligrams of sweat per 20 minutes per axilla, the study is discontinued and the experiment rescheduled for a later time. Subjects with baseline perspiration levels below 150 milligrams of sweat per 20 minutes per axilla are not eligible to proceed into the treatment period.

Each test participant enters the hot room for 90 minutes. During a 40 minute warm-up period, unweighed Webril pads are placed in the axillae and discarded just before the start of the first weighed collection. After the warm-up period, two successive 20-minute sweat collections are made from a 3×5 inch oval area within the 4×6 inch treatment defined area in the axillae. Tared Webril pads (4×6 inches) are folded over a 4×6 inch supporting strip of polyethylene film. A 6×8 inch flannel waterproof sheeting with a 3×5 inch oval cut-out is placed over the Webril pad so that only a 3×5 inch oval area of the Webril pad actually contacts the skin of the axilla. This sweat collection unit is then carefully placed in the axillary vault and held in place during the 20 minute collection period by having each participant hold their arms tightly against their sides.

At the completion of each 20 minute collection period, the Webril pad from each axilla is returned to its original polystyrene vial and tightly capped. These vials and their respective Webril pads are weighed before and after sweat collection. The vials are labeled with the participant's number, axilla, and the collection designation. To prevent incorrect assembly of the vial, cap and pad after use, all three components of the right collection unit are distinctly marked.

The subjects are required to walk about the room at a normal pace during the two 20-minute collection periods. They are permitted to sit during the warm-up period and during a 10-minute rest period between collections. Subjects are also permitted to drink water ad libitum only during the warm-up and rest periods. Water intake is not permitted during the collection periods.

Data collected during the applied methodology is evaluated by statistical analyses, which is described in Wooding, W. M. and Finkelstein, P. A. A critical comparison of two procedures for antiperspirant evaluation. J. Soc. Cosmet. Chem. (1975); 26:225–275; and in Murphy, T. D. and Levine, M. J. Analysis of antiperspirant efficacy test results. J. Soc. Cosmet. Chem. (1991); 42:167–197, which descriptions are incorporated herein be reference. The amount (mg) of sweat collected and the base ten logarithmic value of each such amount is computed and an analysis of covariance is performed with baseline as a covariant. Arm, treatment, group, and subject (within group) are the factors. The group variable defines the treatment sequences assignment to left and right arms. Differences are considered statistically significant at a p-value $\leq 0.05$.

The control product for use in the antiperspirant efficacy methodoloy is a solid antiperspirant wax stick having a product hardness of from 1500 gram·force to 2100 gram·force. The ingredients in the product are listed in Table 1.

TABLE 1

Control Product- Antiperspirant Efficacy Index

| Ingredient | Concentration (wt/wt %) |
| --- | --- |
| Aluminum Zirconium Trichlorohydrex Gly. Summit AAZG-7156 powder, mfr lot #7165118367 | 20.00 |
| Cyclopentasiloxane | 50.685 |
| Stearyl Alcohol | 11.00 |
| Talc, USP Grade | 11.00 |
| Dimethicone (50 csk) | 3.00 |
| Hydrogenated Castor Oil (Castor Wax MP 80, supplied by NL Industries) | 2.90 |
| Fumed Silica (Cab-O-Sil HS-5, supplied by Cabot Corp) | 0.18 |
| Dipropylene Glycol | 0.18 |
| Microthene | 0.18 |
| Behenyl Alcohol | 0.075 |
| Fragrance | 0.80 |

The Antiperspirant Efficacy Index is then calculated as the weight ratio of the amount (mg) of sweat collected from the control treatment side of a participant to the amount of sweat collected from the test product treatment side of that same participant. These calculations are applied to sweat collections at three (3) and/or ten (10) days of concurrent product and control 20 treatment to provide either a 3-day and/or a 10-day Antiperspirant Efficacy Index. Unless otherwise specified, the term "Antiperspirant Efficacy Index" as used herein shall mean the 3-day and/or the 10-day Antiperspirant Efficacy Index.

It has been found that the 10-day Antiperspirant Index of the compositions of the present invention is preferably at least about 0.9, more preferably at least about 1.0, even more preferably at least about 1.1. The 3-day Antiperspirant Index of the compositions of the present invention is preferably at least 1.0, more preferably at least about 1.1, even more preferably at least about 1.2.

It has also been found that the compositions of the present invention are surprisingly more effective after three days of continuous daily application, and that the ratio of the Antiperspirant Index at 3-days and 10-days is preferably greater than or equal to about 0.9, even more preferably greater than or equal to about 1.0, and even more preferably greater than about 1.1. Unlike many other antiperspirant products that require several days of repeated use to develop optimal antiperspirant efficacy, it has been found that the compositions of the present invention provide better antiperspirant efficacy after 3-days of continuous daily application than many other highly effective products and product forms after the same period of application.

II. Essential Ingredients

The anhydrous antiperspirant stick compositions of the present invention are further defined in terms of the combination of essential ingredients as described in detail hereinafter, wherein these select combinations are preferably substantially free of all organic nonvolatile liquids having a C log P value greater than 5.5.

High C log P Liquids

The anhydrous antiperspirant stick compositions of the present invention are preferably substantially free of all organic nonvolatile liquids having a C log P value greater than 5.5, more preferably greater than 6.5, even more preferably greater than 7.0.

In this context, the term "substantially free" means that the compositions preferably contain a sufficiently low concentration of the high C log P organic nonvolatile liquids so that antiperspirant efficacy and/or release is not inhibited. More preferably, the term "substantially free" means that the compositions contain less than 5%, even more preferably less than 2%, even more preferably less than 1%, most preferably zero percent, by weight of the high C log P organic nonvolatile liquids in the antiperspirant stick composition. In this context, the term "organic liquid" means non-silicone containing materials that are liquid at or below human skin temperature under ambient conditions, or which are otherwise in liquid form at or below human skin temperature once formulated into the finished anhydrous antiperspirant stick composition of the present invention.

It has been found that the antiperspirant efficacy of the solid antiperspirant sticks of the present invention are significantly enhanced by maintaining an anhydrous matrix that is substantially free of any nonvolatile organic material that is liquid at or below human skin temperature (37° C.), and which has a relatively high C log P value. It is believed that these materials can hamper dissolution and release of antiperspirant active into sweat ducts after topical application to the skin.

Non limiting examples of organic, high C log P, nonvolatile liquids to which this preferred negative limitation applies includes mineral oil, PPG-14 butyl ether, isopropyl myristate, butyl stearate, cetyl octanoate, butyl myristate, C12–15 alkylbenzoate (e.g., Finsolv™), octyldodecanol, isostearyl isostearate, octododecyl benzoate, isostearyl lactate, isostearyl palmitate, and isobutyl stearate. The compositions of the present invention are preferably substantially free of all nonvolatile, organic liquids that are esters, hydrocarbons, hydroxy substituted hydrocarbons, and combinations thereof, which have the high C log P values described greater herein.

It has been found that the antiperspirant compositions of the present invention are preferably substantially free of these high C log P, nonvolatile, organic liquids but that high C log P organic materials can be used in the compositions provided that such materials are solids at or below human skin temperature (37° C.) or that such materials are physically or chemically partitioned away from the antiperspirant active in the composition, e.g. encapsulation, emulsification, etc. It has been found that such solids or otherwise partitioned materials do not have the same negative effect on antiperspirant efficacy as do the high C log P, nonvolatile, organic liquids described herein.

The use of C log P values is well known in the chemical arts as a calculated value that represents the relative affinity that a material has for partitioning between octanol and water, so that a material that partitions more readily into octanol would tend to be more lipophilic and have a higher C log P value than a material that partitions less readily into octanol. For purposes of defining the antiperspirant compositions of the present invention, C log P values are obtained from or calculated by the methods described in Handbook of Physical Properties of Organic Chemicals, Edited by Philip H. Howard and William M. Meylan, CRC Press- Lewis Publishers, 1997, which description is incorporated herein by reference.

C log P values can also be determined by the Pamona Med Chem/Daylight "C LOG P" program, Version 4.42, available from Biobyte Corporation, Claremont, Calif. Other suitable methods for determining C log P values include the fragment approach described by Hansch and Leo (cf., A. Leo, in Comprehensive Medicinal Chemistry, Vol. 4, C. Hansch, P. G. Sammens, J. B. Taylor and C. A. Ramsden, Eds., p. 295, Pergamon Press, 1990), which description is incorporated herein by reference. Still other suitable methods are described or provided by Daylight Information Systems, Mission Viejo, Calif., Daylight V4.61, Algorithm: V3.05, Database: V16. General information pertaining to C log P values and methodologies are described in Chemical Reviews, 93(4), 1993, 1281–1306, which description is also incorporated herein by reference. As used herein, C log P values include calculated and measured log P values.

The nonvolatile, high C log P, organic liquids may include materials that are solid under ambient conditions but that are at least partially melted and in liquid form at or below human skin temperature (37° C.) or which are otherwise in liquid form in the antiperspirant composition as applied topically to the skin. In this context, a material is determined to be liquid at or below human skin temperature by evaluating the material in a finished antiperspirant composition using Differential Scanning Calorimetry (DSC). For example, A Perkin Elmer Model DSC-7 manufactured by Perkin Elmer Corporation, 761 Main Street, Norwalk Conn., can be used to measure a melting profile of the desired material This is done by preparing a 20 mg sample in a volatile sample pan arrangement of the desired finished product to be tested. The heating curve is generated at 5° C./min and is analyzed by measuring the partial area that melts below 37° C., and those showing at least 10% of the DSC curve below 37° C. are "liquids" for purposes of defining the term "organic liquids" herein.

Antiperspirant Active

The anhydrous antiperspirant stick compositions of the present invention comprise a particulate antiperspirant active suitable for application to human skin. The concentration of antiperspirant active in the composition should be sufficient to provide the desired perspiration wetness and odor control from the antiperspirant stick formulation selected.

The anhydrous antiperspirant stick compositions of the present invention preferably comprise antiperspirant active at concentrations of from about 0.5% to about 60%, more preferably from about 5% to about 35%, by weight of the composition. These weight percentages are calculated on an anhydrous metal salt basis exclusive of water and any complexing agents such as glycine, glycine salts, or other complexing agents. The antiperspirant active as formulated in the composition are in the form of dispersed particulate solids having a preferred average particle size or diameter of less than about 100 μm, preferably less than about 20 μm, even more preferably less than about 10 μm.

The antiperspirant active for use in the anhydrous antiperspirant compositions of the present invention include any compound, composition or other material having antiperspirant activity. Preferred antiperspirant actives include astringent metallic salts, especially inorganic and organic salts of aluminum, zirconium and zinc, as well as mixtures thereof. Particularly preferred are aluminum-containing and/or zirconium-containing salts or materials, such as aluminum halides, aluminum chlorohydrate, aluminum hydroxyhalides, zirconyl oxyhalides, zirconyl hydroxyhalides, and mixtures thereof.

Preferred aluminum salts for use in the anhydrous antiperspirant stick compositions include those which conform to the formula:

$$Al_2(OH)_aCl_b \cdot xH_2O$$

wherein a is from about 2 to about 5; the sum of a and b is about 6; x is from about 1 to about 6; and wherein a, b, and x may have non-integer values. Particularly preferred are the aluminum chlorohydroxides referred to as "5/6 basic chlorohydroxide", wherein a=5, and "2/3 basic chlorohydroxide", wherein a=4. Processes for preparing aluminum salts are disclosed in U.S. Pat. No. 3,887,692, Gilman, issued Jun. 3, 1975; U.S. Pat. No. 3,904,741, Jones et al., issued Sep. 9, 1975; U.S. Pat. No. 4,359,456, Gosling et al., issued Nov. 16, 1982; and British Patent Specification 2,048,229, Fitzgerald et al., published Dec. 10, 1980, all of which are incorporated herein by reference. Mixtures of aluminum salts are described in British Patent Specification 1,347,950, Shin et al., published Feb. 27, 1974, which description is also incorporated herein by reference.

Preferred zirconium salts for use in the anhydrous antiperspirant stick compositions include those which conform to the formula:

$$ZrO(OH)_{2-a}Cl_a \cdot xH_2O$$

wherein a is from about 1.5 to about 1.87; x is from about 1 to about 7; and wherein a and x may both have non-integer values. These zirconium salts are described in Belgian Patent 825,146, Schmitz, issued Aug. 4, 1975, which description is incorporated herein by reference. Particularly preferred zirconium salts are those complexes which additionally contain aluminum and glycine, commonly known as ZAG complexes. These ZAG complexes contain aluminum chlorohydroxide and zirconyl hydroxy chloride conforming to the above described formulas. Such ZAG complexes are described in U.S. Pat. No. 3,679,068, Luedders et al., issued Feb. 12, 1974; Great Britain Patent Application 2,144,992, Callaghan et al., published Mar. 20, 1985; and U.S. Pat. No.

4,120,948, Shelton, issued Oct. 17, 1978, all of which are incorporated herein by reference.

Solid Suspending Agent

The anhydrous antiperspirant stick compositions of the present invention comprise a relatively high concentration of a solid suspending agent to help provide the compositions with the desired viscosity, rheology, texture and/or product hardness, or to otherwise help suspend any dispersed solids or liquids within the composition.

The term "suspending agent" as used herein, unless otherwise specified, means any material known or otherwise effective in providing suspending, gelling, viscosifying, solidifying and/or thickening properties to the composition or which otherwise provide structure to the final product form. These suspending agents include gelling agents, and polymeric or nonpolymeric or inorganic thickening or viscosifying agents. Such materials will typically be solids under ambient conditions and include organic solids, silicone solids, crystalline or other gellants, inorganic particulates such as clays or silicas, or combinations thereof. It especially important that these materials be solids when at or below body temperature when such materials also have a relatively high C log P value of greater than about 5.5.

The concentration and type of suspending agent selected for use in the antiperspirant compositions will vary depending upon the desired product hardness, rheology, and/or other related product characteristics. For most suspending agents suitable for use herein, the total suspending agent concentration ranges from about 16% to about 50%, more typically from about 18% to about 35%, preferably from about 22% to about 35%, by weight of the composition.

Nonlimiting examples of suitable suspending agents include hydrogenated castor oil (e.g., Castorwax MP80, Castor Wax, etc.), solid paraffins, silicone and modified silicone waxes, and combinations thereof, at concentrations ranging from about 1% to about 50%, preferably from about 3% to about 25%, even more preferably from about 5% to about 15%, by weight of the product. These suspending agents when used at concentrations less than about 16% by weight of the composition, will be used in combination with other suitable suspending agents so that the total suspending agent concentration in the composition ranges from about 16% to about 50% by weight of the composition.

Nonlimiting examples of silicone or modified silicone waxes suitable for use as suspending agents herein include alky methyl siloxane wax having the formula R—(SiMe$_2$—O—)$_x$SiMe$_2$R, wherein R is a C16–C40 alkyl group, X is 10 to 50, and Me is a methyl group and the average terminal alkyl chain length is at least C30. Preferably, R is a C25–C40 alkyl group.

Other nonlimiting examples of silicone or modified silicone waxes suitable for use as suspending agents herein include alkyl ester siloxane wax having the formula (Me$_3$Si)O(SiMe$_2$O)$_a$Si(Me)(CH$_2$)$_b$—O—COR(SiMe$_3$), wherein a is an integer from 0 to 2, b is an integer from 2 to 4, Me is methyl, and R is a straight or branched chain alkyl from Cl$_{10}$H$_{21}$ to C$_{30}$H$_{61}$.

Still other nonlimiting examples of silicone or modified silicone waxes suitable for use as suspending agents herein include polyalkylmethylsiloxane waxes such as those corresponding to the formula (CH$_3$)$_3$Si—[O—Si(R$_1$)(CH$_3$)]y—[O—Si(R$_2$)(CH$_3$)]$_z$—O—Si(CH$_3$)$_3$, wherein R$_1$ is a straight chain alkyl group containing from 14 to 22 carbon atoms, R$_2$ is a branched alkyl group containing from 14 to 22 carbon atoms, y+z is from 50 to 80 and z/(y+z) ranges from 0.25 to 0.4.

Specific nonlimiting examples of silicone or modified silicone waxes suitable for use herein include C30–45 alkyl dimethicone or GE SF1642 wax from General Electric Company (alkylmethylsiloxane with the main alkyl species being C30, C32 and C34 with minor amounts of C26 and C28; average terminal chain length is at least C30).

Other nonlimiting examples of suspending agents suitable for use herein are described in U.S. Pat. No. 5,976,514 (Guskey et al.), U.S. Pat. No. 5,891,424 (Bretzler et al.), which descriptions are incorporated herein by reference.

Preferred Suspending Agent

The suspending agents for use in the anhydrous antiperspirant stick compositions of the present invention preferably comprises a solid triglyceride gellant, wherein the solid triglyceride gellant is substantially free of long range crystalline order as formulated within the composition. Any triglyceride gellant that is known or otherwise effective for use in topical products is preferred for use herein, provided that it can also be formulated to have the requisite long range crystalline order within the composition. The concentration of the preferred triglyceride gellants in the composition ranges from about 1% to about 60%, more preferably from about 5% to about 30%, even more preferably from about 10% to about 26%, by weight of the composition, wherein the total gellant concentration in the composition always remains at least about 15% by weight of the composition.

The preferred triglyceride gellant for use in the composition should be a solid at or above human skin temperature (37° C.), either inherently (preferred) or as formulated within the finished composition. The solid triglyceride gellant are preferably and inherently polymorphic, and are capable of being formulated into the composition as a solid matrix that is substantially free of long range crystalline order. Solid triglyceride gellants that have the above-described characteristics will most typically be unsubstituted triglycerides or mixtures of unsubstituted triglycerides that correspond to the following formula:

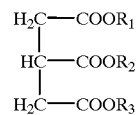

wherein R1, R2 and R3 are the same or different, and are unsubstituted hydrocarbon moieties that are preferably in the form of saturated alkyl groups. These solid triglycerides will most typically be in the form triglyceride mixtures wherein RI, R2 and R3 are alkyl groups having from 2 to 30 carbon atoms, and wherein the average number of carbon atoms per alkyl group per triglyceride molecule [(R1+R2+R3)/3] ranges from about 16 to about 24, more preferably from about 18 about 22.

These solid, unsubstituted, triglyceride gellants are most typically obtained or derived from fully hydrogenated fats characterized as: (1) vegetable fats and oils such as soybean, corn, sunflower, high erucic acid rapeseed, low erucic acid rapeseed, canola, crambe, meadowfoam, cottonseed, olive, safflower, sunflower, sesame seed, nasturtium seed, tiger seed, ricebran, wallflower, and mustard seed; (2) meat fats such as tallow or lard; (3) marine oils such as menhaden, pilcherd, sardine, whale or herring; (4) nut fats and oils such as coconut, palm, palm kernel, babassu kernel, or peanut, Chinese Vegetable Tallow; (5) milkfat, butterfat; (6) cocoa butter and cocoa butter substitutes such as shea, or illipe butter; (7) structured triglycerides fats made from natural and synthetic routes; and (8) synthetic triglycerides made from hydrocarbon sources.

Specific nonlimiting examples of solid, unsubstituted triglyceride gellants suitable for use herein include tristearin, fully hydrogenated high erucic acid rapeseed oil (e.g., HEAR Oil, CanAmera, Canada), fully hydrogenated CRAMBE oil, and tribehenin (e.g., Syncrowax HR-C, Croda, Inc., New York, N.Y., USA). Most preferred is fully hydrogenated high erucic acid rapeseed oil.

The solid triglyceride gellants described herein preferably represent at least about 50%, more preferably at least about 75%, by weight of the total gellant concentration in the composition.

It is believed that at least most of the preferred solid triglycerides described above do not inherently form the desired crystalline phase within the antiperspirant and deodorant composition or do not otherwise form and remain within the desired crystalline phase over extended periods of time. The preferred triglyceride embodiments of the present invention contain the requisite crystalline phase and maintain or are formulated to maintain that phase over prolonged periods of time, so that the product will remain substantially free of long range crystalline order over periods of time ranging from 1, 2, 3, 6, 12 and/or even 24 months after formulation and packing, so that the product remains substantially free of long range crystalline order over any time interval thereof, e.g. at any time between 2 and 12 months after formulation. In maintaining their intended crystalline form, these compositions also maintain or are formulated to maintain their product hardness value at the desired level at any of the time intervals listed above, such that the product hardness for the product preferably does not change by more than about 200 gram·force, more preferably does not change by more than about 100 gram·force, as measure at 1 and 6 months, more preferably as measured at 1 and 3 months, even more preferably as measured at 1 and 2 months after formulation, or over any 1, 2 or 3 month interval within the first 12 months after formulation.

Any known or otherwise effective method of formulating triglyceride solids to be substantially free of long range crystalline order can be applied to the formulation and manufacture of the antiperspirant and deodorant compositions of the present invention. Such methods are well known in the edible fat and shortening arts, although it is believed that their reapplication to antiperspirant and deodorant sticks has not heretofore been described. Examples of suitable methods are described in greater detail hereinafter.

X-ray Diffraction Methodology

The triglyceride crystalline phase within the triglyceride embodiments of the present invention is determined in accordance with the following x-ray diffraction methodology. The various techniques used in the methodology are generally well known in the analytical arts, and are used herein to identify and quantify long range triglyceride crystalline order in the preferred triglyceride embodiments of the present invention.

The following x-ray equipment is used in the diffraction methodology: (1) Philips PW1830 HT Generator w/PW1821 Multi-purpose Sample Stage, (2) Philips PW1397/60 Theta/2-Theta drive and Scintillation Counter, and (3) Philips PW1877 Automated Powder Diffraction Software Program v. 3.5B. Specific instrument parameters are set to divergence slit-¼°; scatter slit ¼°; mask 10 mm; receiving slit 0.05 mm; sample holder 15 mm×20 mm (Philips p/n PW1172); step size 0.05° 2-theta; start angle 1° 2-theta; end angle 3° 2-theta; time per step 10 sec; anode Cu; generator tension 45 kV; and generator current 40 mA.

A external reference standard for use in the methodology is prepared by heating a tribehenin sample (99% tribehenin; Sigma T-7904, Lot# 99H5180) in a 105° C. oven until completely melted. While still molten, the melted tribehenin is then placed in a dewer containing liquid nitrogen until completely solid. The solidified tribehenin is ground to a fine powder using a mortar and pestle. The fine tribehenin powder is placed into a 15 mm×20 mm sample holder (Philips p/n PW1172) and pressed into the holder using a glass microscope slide. All of the excess sample is removed using a knife edge. The holder containing the prepared sample, which is now the external reference standard, is then examined to make sure the surface of the sample is flush with the top of the holder prior to obtaining the x-ray diffraction pattern of the newly prepared external reference standard.

The composition of the present invention, or any other product for evaluation hereunder, is then prepared for x-ray diffraction analysis, and the results of which are then compared to the x-ray diffraction pattern for the external reference standard. The product or composition for analysis is first placed into a 15 mm×20 mm sample holder (Philips p/n PW1172) and then pressed into the holder using a glass microscope slide. The holder is then examined to assure that the sample is flush with the top of the holder prior to obtaining an x-ray diffraction pattern.

X-ray diffraction patterns are obtained for each product sample of interest, and then compared and evaluated relative to the x-ray diffraction pattern of the external reference standard described hereinbefore. The x-ray diffraction patterns are recorded and evaluated for each product sample in terms of peak area and height information by importing the x-ray diffraction patterns of both the external reference standard and the product sample of interest into a BioRad WinIR software package, v. 4.14 Level II, assigning a best fit baseline to the curve(s), integrating the area under the curve(s), and measuring the height of the curve(s), between 1 and 3 degrees 2-theta.

The triglyceride gellant described herein is substantially free of long range crystalline order, wherein such order or the absence of it is characterized by the x-ray diffraction analysis described herein. The product containing the triglyceride gellant is considered for purposes of defining the compositions of the present invention to be substantially free of long range crystalline order with respect to the triglyceride gellant material therein when any one or more of the following x-ray diffraction characteristics is noted.

In one embodiment of the antiperspirant and deodorant compositions of the present invention, the triglyceride gellant and/or product containing the triglyceride gellant is characterized as substantially free of long range crystalline order by an average AUC (area under the curve) at between 1° and 3° 2-theta that is less than about 6%, preferably less than about 5%, more preferably less than about 4%, of the corresponding average AUC for the external reference standard. In this context, the average AUC is determined for the sample product and for the external reference standard from a 10 sample average, each sample being prepared as described herein.

In yet another embodiment of the antiperspirant and deodorant compositions of the present invention, the triglyceride gellant and/or product containing the triglyceride gellant is characterized as substantially free of long range crystalline order by an average peak height at between 1° and 3° 2-theta of less than about 4%, preferably less than about 3%, even more preferably less than about 2%, of the corresponding average peak height of the external reference standard. In this context, the average peak height is determined for the product sample and for the external reference standard from a 10 sample average, each sample being prepared as described above.

The x-ray diffraction characteristics described herein, including average AUC and peak height values described above, must be obtained from the triglyceride gellant and/or product containing the gellant at 3 months, preferably 4 months, more preferably at 6 months after formulation and packaging.

Volatile Silicone

The anhydrous antiperspirant stick compositions of the present invention comprise a volatile silicone carrier. These may be cyclic, linear and/or branched chain silicones having the requisite volatility as defined herein. The concentration of volatile silicone in the antiperspirant composition of the present invention ranges from about 10% to about 80%, preferably from about 20% to about 60%, more preferably from about 30% to about 60%, by weight of the composition.

The volatile silicone is preferably a cyclic silicone having from about 3 to about 7, more preferably from about 5 to about 6, silicon atoms. Most preferred are those which conform to the formula:

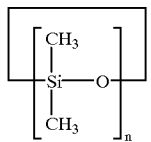

wherein n is from about 3 to about 7, preferably from about 5 to about 6, most preferably 5. These volatile cyclic silicones generally have a viscosity of less than about 10 centistokes. Suitable volatile silicones for use herein include, but are not limited to, Cyclomethicone D5 (commercially available from G. E. Silicones); Dow Corning 344, and Dow Corning 345 (commercially available from Dow Corning Corp.); and GE 7207, GE 7158 and Silicone Fluids SF-1202 and SF-1173 (available from General Electric Co.).

Nonlimiting examples of suitable volatile silicones are described in Todd et al., "Volatile Silicone Fluids for Cosmetics", Cosmetics and Toiletries, 91:27–32 (1976), which descriptions are incorporated herein by reference.

Nonvolatile Silicone

The anhydrous antiperspirant compositions of the present invention further comprise a non-volatile silicone carrier. The non volatile silicone may be a solid (e.g., silicone wax) or liquid, but is most preferably a liquid at or below human skin temperature. The concentration of the non volatile silicone is from about 1% to about 35%, more preferably from about 5% to about 30%, by weight of the composition.

The non volatile silicone carrier is preferably a liquid at or below human skin temperature, or otherwise in liquid form within the anhydrous antiperspirant composition during or shortly after topical application. Preferred are those nonvolatile liquid silicones which conform to either of the formulas:

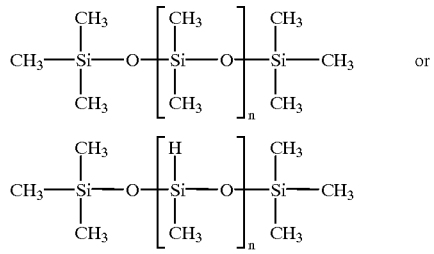

wherein n is sufficiently large to provide a viscosity of up to about 100,000 centistokes, preferably less than about 500 centistoke, more preferably from 10 centistoke to about 200 centistoke, even more preferably from 10 centistoke to about 50 centistoke, as measured under ambient conditions.

Specific non limiting examples of suitable non volatile, linear, silicone carriers include Dow Corning 200, hexamethyldisiloxane, Dow Corning 225, Dow Corning 1732, Dow Corning 5732, Dow Corning 5750 (available from Dow Corning Corp.); and SF-96, SF-1066 and SF18 (350) Silicone Fluids (available from G.E. Silicones).

III. Optional Ingredients

The anhydrous antiperspirant compositions of the present invention may further comprise any optional material that is known for use in antiperspirant and deodorant compositions or other personal care products, or which is otherwise suitable for topical application to human skin, provided that such optional material is not an organic nonvolatile liquid as described herein having a relatively high C log P value.

Nonlimiting examples of optional materials include dyes or colorants, emulsifiers, perfumes, distributing agents, antimicrobials, deodorant perfumes, pharmaceutical or other topical active, preservatives, surfactants, processing aides such as viscosity modifiers, wash-off aids, and so forth. Examples of such optional materials are described in U.S. Pat. No. 4,049,792 (Elsnau); U.S. Pat. No. 5,019,375 (Tanner et al.); and U.S. Pat. No. 5,429,816 (Hofrichter et al.); which descriptions are incorporated herein by reference.

Other suitable optional materials include solid and/or liquid carriers other than and in addition to the volatile and non volatile silicones described herein. An example of such other optional carrier includes volatile nonpolar, hydrocarbon liquids, preferably at concentrations ranging from about 1% to about 40%, preferably from about 1% to about 20%, by weight of the composition. The volatile, nonpolar, hydrocarbon liquids can have a cyclic, branched and/or :chain configuration, and can be saturated or unsaturated, preferably saturated. Preferred among these hydrocarbon liquids are volatile, branched chain hydrocarbons having from about 6 to about 40 carbon atoms, preferably from about 6 to about 20 carbon atoms. These volatile hydrocarbon liquids will most typically be formulated as a combination of two or more of the above-described branched chain hydrocarbons, wherein the combination of two or more hydrocarbons have different molecular weights, number of carbon atoms, and/or chain configurations. Specific nonlimiting examples of such combinations include the isoparaffins available from Exxon Chemical Company, Baytown, Tex. U.S.A, sold as Isopar M (C13–C14 Isoparaffin), Isopar C (C7–C8 Isoparaffin), Isopar E (C8–C9 Isoparaffin), Isopar G (C10–11 Isoparaffin), Isopar L (C11–C13 Isoparaffin), Isopar H (C11–C12 Isoparaffin), and combinations thereof. Other nonlimiting examples of suitable branched chain hydrocarbons include Permethyl 99A (C12, isododecane), Permethyl 101A (C16, isohexadecane), Permethyl 102A (C20, isoeicosane), and combinations thereof. The Permethyl series are available from Presperse, Inc., South Plainfield, N.J., U.S.A. Other nonlimiting examples of suitable branched chain hydrocarbons include petroleum distillates such as those available from Phillips Chemical as Soltrol 130, Soltrol 150, Soltrol 170, and those available from Shell as Shell Sol-70, -71, and -2033.

Still other suitable isoparaffins include C9–C11 Isoparaffin, C9–C13 Isoparaffin, C9–C14 Isoparaffin, C10–C13 Isoparaffin, C12–C14 Isoparaffin, C13–C16 Isoparaffin, C14–C18 Isoparaffin, and hydrogenated polyisobutene available from Amoco as the Panalane Series and from Fanning Corporation as the Fancor P series.

Nonlimiting examples of other volatile, nonpolar hydrocarbon liquids suitable for use in the antiperspirant and deodorant compositions include paraffins such as dodecane, octane, decane and combinations thereof, and the Norpar series of paraffins available from Exxon Chemical Company such as Norpar-12, -13, and -15 and the Neosolve series of paraffins available from Shell. Yet another example includes C11–C15 alkanes/cycloalkanes, such as those available from Exxon as Exxsol D80.

IV. Methods of Manufacture

The anhydrous antiperspirant stick compositions of the present invention may be prepared by any known or otherwise effective technique, suitable for formulating an antiperspirant stick composition having the product characteristics described herein.

For example, the antiperspirant stick compositions can be formulated by mixing the volatile and nonvolatile silicone materials under ambient conditions, or under conditions sufficient to render the admixture fluid or liquid, and then adding any suspending agents to the mixture and heating the resulting mixture sufficiently to liquefy the added suspending agents, e.g., approximately 85° C. for many wax solids, and form a single phase liquid. Antiperspirant solids are then added to and dispersed throughout the heated, single phase liquid before allowing the resulting combination to cool to approximately 78° C., at which point perfumes and similar other materials (if any) are mixed into the combination, which is then cooled to just above the solidification point of the suspending agent (e.g., typically about 60° C.) and then poured into dispensing packages and allowed to solidify under ambient conditions.

In yet another example, a 100 gram batch of product is prepared by combining in a 250 ml container fully hydrogenated HEAR oil (15 gm), Syncrowax HGLC (3.75 gm), cyclopentasiloxane (46.25 gm), Isopar M (10 gm), and 50 cs dimethicone (5 gm). The ingredients are heated with agitation on an IKA RET control viscosity stir plate to 85° C., with the agitation set at 400 rpm. Once the combined ingredients reach 85° C., aluminum zirconium trichlorohydrex glycinate (20gm) (Westchlor ZR 60B DM HBD Powder) are added with agitation while maintaining the temperature at 85° C., after which the resulting combination is milled to break-up and mechanically disperse any clumps of antiperspirant active using an IKA Ultra Turrax T25 dispersator with an 18G model dispersing tool. The dispersator is set at 5 speed and allowed to run for about 2 minutes or until there are no visible lumps of undispersed active (seen by placing a metal spatula in the beaker and looking for nodules of active on the spatula). The combined ingredients are then cooled with agitation on the IKA hotplate (in a hood with an air velocity of about 100–130 cubic ft./min) from 85° C. to about 65° C. with the hood left partly (6–12 inches) open. On reaching 65° C., the beaker is then removed from the hotplate and the mixture rapidly poured into an antiperspirant stick package inside the hood with the hood left partly (6–12 inches) open. The stick is allowed to set-up undisturbed in the hood for about 20–30 minutes. The stick may then be stored under ambient conditions or under any other selected condition helpful to complete the development of the optimal crystalline structure within the finished product. The optimum structure is developed within the finished product about 7 days after formulation and solidification, wherein the optimized structure helps provide the desired residue, cosmetic, and efficacy characteristics of the finished product.

Nonlimiting examples of other suitable manufacturing methods are described in U.S. Pat. No. 4,822,603 (Farris et al.), which descriptions are incorporated herein by reference.

V. Methods of Manufacture-preferred Triglyceride Embodiments

The triglyceride embodiments of the antiperspirant and deodorant stick compositions of the present invention may be prepared by any known or otherwise effective technique, suitable for providing an antiperspirant stick composition having the product characteristics described herein, preferably by any method that also includes control over the crystalline phase of the triglyceride gellant so that the triglyceride gellant as formulated into the composition is substantially free of long range crystalline order as described herein.

A preferred method for controlling the crystalline phase of the triglyceride gellant of the preferred triglyceride embodiments herein is by the addition and use of materials that are well known for or otherwise effective in retarding phase transitions in triglycerides. Examples of such materials and use are generally described in "Crystallization And Polymorphism Of Fats and Fatty Acids" edited by Nissim Garti and Kiyotaka Sato, volume 31 (1988), which description is hereby incorporated by reference. Specific non-limiting examples of such materials include surfactants, emulsifiers, C14–26 fatty acids, C12–30 monoglycerides and/or C12–30 diglycerides, fully and partially esterified polyglycerol esters and derivatives thereof, sorbitan esters and derivatives thereof (e.g., sorbitan tristearate, sorbitain monostearate, sorbitan monopalmitate), dibenhenate and/or distearine, behenic acid, stearic acid, lecithin and fractions of lecithin, structured forms of mono and diglycerides, mixtures of saturated triglycerides and their breakdown components made through enzymatic digestion or other cleavage/cracking processes, structured mono, diglyceride and triglyceride mixtures synthesized from hydrocarbons, and combinations thereof.

Especially preferred for controlling triglyceride crystallization in the preferred triglyceride embodiments herein include the use of fully hydrogenated BEAR oil (high erucic acid rape seed oil) with Syncrowax HGLC (C18–36 Acid Triglyceride) at a weight ratio of from about 4:1 to about 1:1. Other preferred materials include fully hydrogenated BEAR oil in combination with dibehenin (Compritol 888, manufactured by Gattefosse) at a weight ratio of from about 4:1 to about 1:1, and fully hydrogenated HEAR oil in combination with HEAR oil mono and diglycerides at a weight ratio of from about 4: 1 to about 1:1. Most preferred is the combination of fully hydrogenated BEAR oil and Syncrowax HGLC at a weight ratio of about 4:1, wherein the composition contains 15% by weight of the fully hydrogenated BEAR and 3.75% by weight of the Syncrowax HGLC.

Another method of controlling the triglyceride crystalline or molecular phase distribution is by controlling the rate of cooling of the liquefied triglyceride solid during formulation so that the peak melting point as measured by DSC (Differential Scanning Calorimetry) for the resulting triglyceride phase in the formulation is between about 57° C. and about 60° C. and the resulting triglyceride gellant in the formulation is substantially free of long range crystalline order as determined by the x-ray phase methodology described herein. Methods for determining DSC values for solid materials are well known in the chemical arts, and can be easily reapplied to the antiperspirant and deodorant compositions of the present invention. For example, a Perkin Elmer Model DSC-7, manufactured by Perkin Elmer Corporation, 761 Main Street, Norwalk Conn., can be used to measure a melting profile of the desired material This is done by preparing a 20 mg sample in a volatile sample pan arrangement of the desired finished product to be tested. The heating curve (DSC curve) is generated at 5° C. per minute.

The triglyceride embodiments of the present invention can be formulated, for example, by mixing the carrier liquid(s) under ambient conditions, or under conditions sufficient to render the admixture fluid or liquid, and adding the triglyceride and other non-active solids to the mixture and then heating the resulting mixture sufficiently to liquefy the added materials and to form a single phase liquid, e.g. 85° C. Antiperspirant solids, if any, are then added to and dispersed throughout the heated, single phase liquid before allowing the resulting combination to cool to approximately 78° C., at which point perfumes or other similar materials are mixed into the combination, which is then allowed to cool to 60° C. which is just above the solidification temperature of the formulation matrix at a cooling rate of from 0.5° C. per minute to 200° C. per minute (rate can be selected to obtain a solidified triglyceride matrix that is substantially free of long range crystalline order) before being poured into dispensing packages and allowed to solidify under ambient or other selected condition to obtain the desired crystalline form of the triglyceride gellant.

VI. Method of Use

The anhydrous antiperspirant stick compositions of the present invention may be applied topically to the axilla or other area of the skin in an amount effective to treat or reduce perspiration wetness and malodor. The composition is preferably applied in an amount ranging from about 0.1 gram to about 20 grams, more preferably from about 0.1 gram to about 10 grams, even more preferably from about 0.1 gram to about 1 gram, to the desired area of the skin. The compositions are preferably applied one to two times daily, preferably once daily, to achieve effective antiperspirant and malodor control over an extended period.

VII. Modified Stick Formulations

The anhydrous antiperspirant stick compositions of the present invention can be modified in the following manner to also provide compositions that deliver low residue performance and improved antiperspirant efficacy.

The modified stick formulation comprises (a) from about 0.5% to about 60% by weight of particulate antiperspirant active; (b) from about 3% to about 50% by weight of a solid suspending agent containing a first suspending agent and a second suspending agent; (c) from about 10% to about 80% by weight of a carrier liquid, preferably a volatile and/or non volatile silicone. The modified stick formulation is anhydrous, has a Tan Delta value of less than about 0.40, is substantially free of nonvolatile organic liquids having a C log P value greater than 5.5 as also described herein or otherwise has an Antiperspirant Efficacy Index as described herein. The modified formulation is in the form of a solid stick having a product hardness as described hereinbefore for the anhydrous antiperspirant stick compositions of the present invention. Except as otherwise described hereinabove specifically for the modified formulation, all other preferred or optional materials, ingredients concentrations, and other product features as described hereinbefore for the anhydrous antiperspirant stick compositions apply to the modified stick formulation described above.

The first and second solid suspending agents of the modified stick formulation are characterized by the following: (a) the first and second suspending agents are solids at human skin temperature (37° C.), (b) the first and second suspending agents together have a melt point of less than 120° C. as measured by DSC within the antiperspirant composition, wherein the second suspending agent has a lower melt point than the first suspending agent, (c) the second suspending agent is liquified during formulation of the antiperspirant composition and then used in liquid form to solubilize within the composition the first suspending agent at a temperature less than 120° C.

The first and second suspending agents can include any suspending agent that is known or otherwise effective for use in personal care products, including the suspending agents described hereinbefore, provided that such first and second suspending agents also have the requisite characteristics as described above for the modified formulation.

The first suspending agent is preferably one or more suspending agents such as diamide and triamide gellants such as those described in U.S. Pat. No. 5,429,816 (Hofrichter et al.), and other relatively high melting point gellants, specific examples of which includes N-lauroyl-L-glutamic acid-di-n-butylamide, 12-hydroxystearic acid, sucrose esters, and combinations thereof.

The second suspending agent is preferably one or more suspending agents such as glycerol esters, propylene glycol esters, sucrose esters, and other relatively low melting point gellants, a specific example of which includes fully hydrogenated high Erucic acid rapeseed oil.

Other optional gellants can also be used in the composition in addition to the first and second gellants described hereinabove.

It has been found that, as described above, it is useful to modify the antiperspirant composition of the present invention so that the modified composition contains a combination of solid suspending agents or other similar solid ingredients that have a higher melting component and a lower melting component, each of which may be comprised of multiple ingredients. The lower melting component is chosen during formulation of the antiperspirant composition so that it helps to solublize the higher melting component in the liquid carrier, without the necessity of using the non volatile, liquid, high C log P solvents as described herein for purposes of solubilizing and coupling the solid suspending agent in the composition.

The combination of solid suspending agents forms a solid matrix within the finished antiperspirant composition, which thus contains within the solid matrix the liquid carrier component, preferably a combination of a volatile and non volatile silicone. In the context of the modified formulations described above, a suspending agent is a solid under human skin temperatures so that the suspending agent combination generates a DSC curve from within the formulation by the methods described or referenced herein, wherein at least 95% of the total melting curve is above human skin temperature.

The term "solubilized" as used in the context of the modified formulation means that a material or combination of materials (e.g., first and second suspending agents) is a single phase liquid under a specified temperature and other conditions, and thus generates a DSC curve wherein 95% of the total melting curve is below the specified temperature under the specified conditions, and wherein the modified formulations (less antiperspirant active and other similar particulate solids that are insoluble during processing and do not otherwise have a melt point less than 250° C.) have a translucent or clear appearance when heated to and mixed at 120° C., thus indicating that the first and second suspending agents have been successfully solubilized as a single phase liquid within the modified formulation during processing. In short, but for the presence of the second suspending agent in the composition, the first suspending agent would not be solubilized to form within the composition during formulation a single phase liquid with the other liquid materials, e.g., liquified gellants, carrier liquids.

A non limiting example of the modified formulation described above is set forth in the following Table 2. All amounts are by weight of the overall modified formulation, unless otherwise specified. The exemplified composition is an anhydrous antiperspirant stick that provides low residue performance and improved antiperspirant efficacy.

TABLE 2

Modified Formulation

| Ingredient | Wt % |
|---|---|
| Al Zr Trichlorohydrex Glycinate | 24.00 |
| Cyclopentasiloxane | 43.05 |
| N-lauroyl-L-glutamic acid-di-n-butylamide | 1.10 |
| 12-Hydroxy Stearic Acid | 3.85 |
| Tribehenin (Syncrowax HR-C) | 10.00 |
| C18–36 Acid Triglyceride (Syncrowax HGLC) | 2.50 |
| C13–14 Isoparaffin (Isopar M) | 10.00 |
| Dimethicone 50 cs | 5.00 |
| Disodium EDTA | 0.50 |
| Residue Grade | 25.82 |
| Product Hardness | 1600 |
| Tan Delta | 0.20 |
| Antiperspirant Index 3-day | 1.19 |
| Antiperspirant Index 10-day | 1.13 |
| % Liquid Gellant at Body Temperature (DSC Method) | 0.03 |

The modified formulation described in Table 2 may be prepared by any known or otherwise effective technique, suitable for formulating an antiperspirant stick or other composition having the product characteristics described herein. As one such example, a 250 gram batch of product is prepared by combining in a 400 ml container the C13–14 Isoparaffin, Dibutyl Lauroyl Glutamide, 12-Hydroxy Stearic Acid, Cyclopentasiloxane, Dimethicone, Tribehenin and C18–36 Acid Triglyceride. The ingredients are heated with agitation on an IKA RET control viscosity stir plate to 120° C. with the agitation set at 400 rpm. Once the solids are dissolved, the aluminum zirconium trichlorohydrex glycinate and disodium EDTA powders are added while maintaining the temperature at 95° C. The combined ingredients are then cooled with agitation on the IKA hotplate (in a hood with an air velocity of about 100–130 cubic ft./min.) from 95° C. to about 75° C. with the hood left partly (6–12 inches) open. On reaching 75° C., the beaker is then removed from the hotplate and the mixture rapidly poured into antiperspirant stick packages inside the hood with the hood left partly (6–12 inches) open. The sticks are allowed to set up undisturbed in the hood for about 20–30 minutes. The sticks may then be stored under ambient conditions or under any other selected condition helpful to complete the development of the optimal crystalline structure within the finished product. The optimum structure is developed within the finished product about 7 days after formulation and solidification, wherein the optimized structure helps provide the desired residue, cosmetic and efficacy characteristics of the finished product.

VIII. Examples

The following non-limiting examples illustrate specific embodiments of the antiperspirant stick compositions of the present invention, including methods of manufacture and use.

Each of the exemplified compositions are prepared by combining all of the listed components except the antiperspirant active and perfume. The combined components are heated to about 85° C. with agitation to form a hot liquid, after which all other materials are added to the heated liquid and the mixture is milled using an IKA Dispersator (as earlier described). The heated liquid is allowed to cool with agitation until just before the point of solidification, at which point the cooled, liquid composition is filled into applicator packages and allowed to cool further and solidify to the requisite product hardness.

Each of the exemplified compositions has a Residue Grade of less than about 35, a product hardness of between about 600 and about 5,000 gram·force, a Tan Delta value at 1 Hz of less than 0.40, and an Antiperspirant Efficacy Index greater than 1.0. Each of the exemplified compositions is applied topically to the axilla area of the skin, in accordance with the methods of use described herein, and provide improved low residue performance and antiperspirant efficacy.

All exemplified amounts are weight percentages based upon the total weight of the antiperspirant stick composition, unless otherwise specified.

TABLE 3

| Ingredient | Example 1 | Example 2 | Example 3 | Example 4 |
|---|---|---|---|---|
| Al Zr Trichlorhydrex Glycinate | 20.00 | 20.00 | 25.25 | 24.00 |
| Cyclopentasiloxane | 45.50 | 45.50 | 40.25 | 41.50 |
| Tribehenin (Syncrowax HR-C)[1] | 0.00 | 15.00 | 15.00 | 15.00 |
| C18–36 Acid Triglyceride (Syncrowax HGLC)[2] | 3.75 | 3.75 | 3.75 | 3.75 |
| Perfume | 0.75 | 0.75 | 0.75 | 0.75 |
| C13–C14 Isoparaffin (Isopar M)[3] | 10.00 | 10.00 | 10.00 | 10.00 |
| Dimethicone 50 cs | 5.00 | 5.00 | 5.00 | 5.00 |
| Fully Hydrogenated High Erucic Acid Rapeseed Oil[4] | 15.00 | 0.00 | 0.00 | 0.00 |
| Totals | 100.00 | 100.00 | 100.00 | 100.00 |
| Residue Grade | 29.1 | 29.0 | 30.5 | 30.8 |
| Product Hardness | 870 | 870 | 1025 | 1050 |
| Tan Delta | 0.2 | 0.2 | 0.22 | 0.21 |
| Antiperspirant Index 3-day | 1.24 | 1.24 | 1.32 | 1.20 |
| Antiperspirant Index 10-day | 1.15 | 1.15 | 1.27 | 1.15 |
| % Liquid Gellant At Body Temperature (DSC Method) | 0.08 | 0.08 | 0.08 | 0.08 |

[1]Croda, Inc., New York, New York, USA
[2]Croda, Inc., New York, New York, USA
[3]Exxon Chemical Company, Baytown, Texas, USA,
[4]CanAmera, Canada

TABLE 4

| Ingredient | Example 5 | Example 6 | Example 7 |
|---|---|---|---|
| Al Zr Trichlorhydrex Glycinate | 25.00 | 25.00 | 20.00 |
| Cyclopentasiloxane | 50.50 | 40.50 | 48.00 |
| Tribehenin (Syncrowax HR-C)[1] | 0.00 | 0.00 | 10.00 |
| C18–36 Acid Triglyceride (Syncrowax HGLC)[2] | 3.75 | 0.00 | 2.50 |
| Fragrance | 0.75 | 0.75 | 0.75 |
| C13–C14 Isoparaffin (Isopar M)[3] | 0.00 | 10.00 | 10.00 |
| Dimethicone 50 cs | 5.00 | 5.00 | 5.00 |
| Fully Hydrogenated High Erucic Acid Rapeseed Oil[4] | 15.00 | 15.00 | 0.00 |
| C18–36 Acid Glycol Ester (Syncrowax ERL-C)[5] | 0.00 | 3.75 | 0.00 |
| Strahl & Pitsch Paraffin SP173[6] | 0.00 | 0.00 | 3.75 |
| Totals | 100.00 | 100.00 | 100.00 |
| Residue Grade | 30.8 | 29.0 | 32.8 |
| Product Hardness | 1050 | 1040 | 956 |
| Tan Delta | 0.18 | 0.2 | 0.18 |
| Antiperspirant Index 3-day | 1.24 | 1.30 | 1.20 |
| Antiperspirant Index 10-day | 1.15 | 1.25 | 1.13 |
| % Liquid Gellant at Body Temperature (DSC Method) | 0.00 | 0.10 | 1.53 |

[1] Croda, Inc., New York, New York, USA
[2] Croda, Inc., New York, New York, USA
[3] Exxon Chemical Company, Baytown, Texas, USA
[4] CanAmera, Canada
[5] Croda, Inc., New York, New York, USA
[6] Strahl & Pitsch, Inc., West Babylon, New York

What is claimed is:

1. An anhydrous antiperspirant stick composition comprising:
   (a) from about 0.5% to about 60% by weight of particulate antiperspirant active;
   (b) from about 16% to about 50% by weight of a solid suspending agent;
   (c) from about 10% to about 80% by weight of a volatile silicone; and
   (d) from about 1% to about 35% by weight of a non volatile silicone;
wherein the composition is anhydrous, has a product hardness of at least about 600 gram·force, has a Residue Grade of less than about 50, and is substantially free of nonvolatile organic liquids having a C log P value greater than about 5.5.

2. The composition of claim 1 wherein the composition comprises less than about 1% by weight of the nonvolatile organic liquid and less than about 1% by weight of free or added water.

3. The composition of claim 2 wherein the composition is substantially free of nonvolatile organic liquids having a C log P value greater than about 7.0.

4. The composition of claim 1 wherein the particulate antiperspirant active is selected from the group consisting of aluminum-containing active, zirconium-containing active, and combinations thereof.

5. The composition of claim 1 wherein the solid suspending agent comprises a solid triglyceride gellant.

6. The composition of claim 5 wherein the solid triglyceride is substantially free of long range crystalline order within the composition as measured at about 6 months after formulation of the composition.

7. The composition of claim 5 wherein the solid triglyceride comprises fully-hydrogenated high erucic acid rapeseed oil.

8. The composition of claim 1 wherein the solid suspending agent comprises hydrogenated castor oil.

9. The composition of claim 1 wherein the solid suspending agent comprises a C30–45 alkyl dimethicone wax.

10. The composition of claim 1 wherein the solid suspending agent comprises a solid paraffin.

11. The composition of claim 1 wherein the volatile silicone is cyclomethicone and the nonvolatile silicone is a liquid at or below 37° C.

12. The composition of claim 1 wherein the composition further comprises from about 1% to about 40% by weight of a volatile, non-polar, branched-chain hydrocarbon liquid.

13. The composition of claim 1 wherein the product hardness ranges from about 800 gram·force to about 1,400 gram·force.

14. The composition of claim 1 wherein the Residue Grade is less than about 35.

15. An anhydrous antiperspirant stick composition comprising:
   (a) from about 0.5% to about 60% by weight of particulate antiperspirant active;
   (b) from about 16% to about 50% by weight of a solid suspending agent;
   (c) from about 10% to about 80% by weight of a volatile silicone; and
   (d) from about 1% to about 35% by weight of a non volatile silicone;
wherein the composition is anhydrous, has a product hardness of at least about 600 gram·force, has a Tan Delta value of less than about 0.40, and is substantially free of nonvolatile organic liquids having a C log P value greater than 5.5.

16. The composition of claim 15 wherein the composition comprises less than about 1% by weight of the nonvolatile organic liquid and less than about 1% by weight of free or added water.

17. The composition of claim 16 wherein the composition is substantially free of nonvolatile organic liquids having a C log P value greater than about 7.0.

18. The composition of claim 17 wherein the particulate antiperspirant active is selected from the group consisting of aluminum-containing active, zirconium-containing active, and combinations thereof.

19. The composition of claim 17 wherein the solid suspending agent comprises a solid triglyceride gellant.

20. The composition of claim 19 wherein the solid triglyceride is substantially free of long range crystalline order within the composition as measured at about 6 months after formulation of the composition.

21. The composition of claim 19 wherein the solid triglyceride comprises fully-hydrogenated high erucic acid rapeseed oil.

22. The composition of claim 17 wherein the solid suspending agent comprises hydrogenated castor oil.

23. The composition of claim 17 wherein the solid suspending agent comprises a C30–45 alkyl dimethicone wax.

24. The composition of claim 17 wherein the solid suspending agent comprises a solid paraffin.

25. The composition of claim 17 wherein the volatile silicone is cyclomethicone and the nonvolatile silicone is a liquid at or below 37° C.

26. The composition of claim 17 wherein the composition further comprises from about 1% to about 40% by weight of a volatile, non-polar, branched-chain hydrocarbon liquid.

27. The composition of claim 17 wherein the product hardness ranges from about 800 gram·force to about 1,400 gram·force.

28. The composition of claim 18 wherein the Residue Grade is less than about 35.

29. An anhydrous antiperspirant stick composition comprising:
(a) from about 0.5% to about 60% by weight of particulate antiperspirant active;
(b) from about 16% to about 50% by weight of a solid suspending agent;
(c) from about 10% to about 80% by weight of a volatile silicone; and
(d) from about 1% to about 35% by weight of a non volatile silicone;

wherein the composition is anhydrous, has a product hardness of at least about 600 gram·force, has a Residue Grade of less than about 50, and has Antiperspirant Efficacy Index of at least about 0.9.

30. The composition of claim 29 wherein the composition comprises less than about 1% by weight of the nonvolatile organic liquid and less than about 1% by weight of free or added water.

31. The composition of claim 30 wherein the composition is substantially free of nonvolatile organic liquids having a C log P value greater than about 7.0.

32. The composition of claim 29 wherein the particulate antiperspirant active is selected from the group consisting of aluminum-containing active, zirconium-containing active, and combinations thereof.

33. The composition of claim 29 wherein the solid suspending agent comprises a solid triglyceride gellant.

34. The composition of claim 33 wherein the solid triglyceride is substantially free of long range crystalline order within the composition as measured at about 6 months after formulation of the composition.

35. The composition of claim 33 wherein the solid triglyceride comprises fully-hydrogenated high erucic acid rapeseed oil.

36. The composition of claim 29 wherein the solid suspending agent comprises hydrogenated castor oil.

37. The composition of claim 29 wherein the composition comprises a C30–45 alkyl dimethicone wax.

38. The composition of claim 29 wherein the solid suspending agent comprises a solid paraffin.

39. The composition of claim 29 wherein the volatile silicone is cyclomethicone and the nonvolatile silicone is a liquid at or below 37° C.

40. The composition of claim 29 wherein the composition further comprises from about 1% to about 40% by weight of a volatile, non-polar, branched-chain hydrocarbon liquid.

41. The composition of claim 29 wherein the product hardness ranges from about 800 gram·force to about 1,400 gram·force.

42. The composition of claim 29 wherein the Residue Grade is less than about 35.

43. The composition of claim 29 wherein the Antiperspirant Efficacy Index is a 10-day Antiperspirant Index of at least about 1.1.

44. The composition of claim 29 wherein the Antiperspirant Efficacy Index is a 3-day Antiperspirant Index of at least about 1.1.

45. The composition of claim 29 wherein the ratio of the Antiperspirant Index at 3-days and 10-days is greater than about 0.9.

46. The composition of claim 29 wherein the ratio of the Antiperspirant Index at 3-days and 10-days is greater than about 1.1.

47. An anhydrous antiperspirant stick composition comprising:
(a) from about 0.5% to about 60% by weight of particulate antiperspirant active;
(b) from about 16% to about 50% by weight of a solid suspending agent;
(c) from about 10% to about 80% by weight of a volatile silicone; and
(d) from about 1% to about 35% by weight of a non volatile silicone;

wherein the composition is anhydrous, has a product hardness of at least about 600 gram·force, has a Tan Delta value of less than about 0.40, and has an Antiperspirant Efficacy Index of at least about 0.9.

48. The composition of claim 47 wherein the composition comprises less than about 1% by weight of the nonvolatile organic liquid and less than about 1% by weight of free or added water.

49. The composition of claim 48 wherein the composition is substantially free of nonvolatile organic liquids having a C log P value greater than about 7.0.

50. The composition of claim 48 wherein the particulate antiperspirant active is selected from the group consisting of aluminum-containing active, zirconium-containing active, and combinations thereof.

51. The composition of claim 48 wherein the solid suspending agent comprises a solid triglyceride gellant.

52. The composition of claim 51 wherein the solid triglyceride is substantially free of long range crystalline order within the composition as measured at about 6 months after formulation of the composition.

53. The composition of claim 50 wherein the solid triglyceride is fully-hydrogenated high erucic acid rapeseed oil.

54. The composition of claim 50 wherein the solid suspending agent comprises hydrogenated castor oil.

55. The composition of claim 50 wherein the solid suspending agent comprises a C30–45 alkyl dimethicone wax.

56. The composition of claim 50 wherein the solid suspending agent comprises a solid paraffin.

57. The composition of claim 50 wherein the volatile silicone is cyclomethicone and the nonvolatile silicone is a liquid at or below 37° C.

58. The composition of claim 50 wherein the composition further comprises from about 1% to about 40% by weight of a volatile, non-polar, branched-chain hydrocarbon liquid.

59. The composition of claim 50 wherein the product hardness ranges from about 800 gram·force to about 1,400 gram·force.

60. The composition of claim 50 wherein the Tan Delta is less than about 0.30.

61. The composition of claim 50 wherein the Antiperspirant Efficacy Index is a 10-day Antiperspirant Index of at least about 1.1.

62. The composition of claim 50 wherein the Antiperspirant Efficacy Index is a 3-day Antiperspirant Index of at least about 1.1.

63. The composition of claim 50 wherein the ratio of the Antiperspirant Index at 3-days and 10-days is greater than about 0.9.

64. The composition of claim 50 wherein the ratio of the Antiperspirant Index at 3-days and 10-days is greater than about 1.1.

* * * * *